(12) United States Patent
Baril et al.

(10) Patent No.: US 12,127,740 B2
(45) Date of Patent: *Oct. 29, 2024

(54) BUTTRESS ATTACHMENT FOR SURGICAL STAPLING APPARATUS

(71) Applicant: Covidien LP, Mansfield, MA (US)

(72) Inventors: Jacob C. Baril, Norwalk, CT (US); Roanit Fernandes, Hyderabad (IN)

(73) Assignee: Covidien LP, Mansfield, MA (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/070,077

(22) Filed: Nov. 28, 2022

(65) Prior Publication Data
US 2023/0091401 A1 Mar. 23, 2023

Related U.S. Application Data

(63) Continuation of application No. 17/355,240, filed on Jun. 23, 2021, now Pat. No. 11,510,670.

(51) Int. Cl.
*A61B 17/072* (2006.01)
*A61B 17/068* (2006.01)

(52) U.S. Cl.
CPC ........ *A61B 17/0686* (2013.01); *A61B 17/072* (2013.01); *A61B 17/07292* (2013.01);
(Continued)

(58) Field of Classification Search
CPC . A61B 17/068; A61B 17/0686; A61B 17/072; A61B 17/07207; A61B 17/07292; A61B 17/115; A61B 2017/00477; A61B 2017/07228; A61B 2017/07271; A61B 2017/07214
(Continued)

(56) References Cited

U.S. PATENT DOCUMENTS

| 3,054,406 A | 9/1962 | Usher |
|---|---|---|
| 3,124,136 A | 3/1964 | Usher |

(Continued)

FOREIGN PATENT DOCUMENTS

| CA | 2282761 A1 | 9/1998 |
|---|---|---|
| DE | 1602563 U | 3/1950 |

(Continued)

OTHER PUBLICATIONS

European Search Report corresponding to EP 06 00 4598, completed Jun. 22, 2006; (2 pp).

(Continued)

*Primary Examiner* — Scott A Smith

(57) ABSTRACT

A surgical stapling apparatus includes a loading unit, a surgical buttress, and a buttress retention band. The loading unit includes an anvil assembly and a staple cartridge assembly. The staple cartridge assembly includes a staple cartridge having a tissue facing surface including staple pockets and a central longitudinal slot defined therethrough, and a protrusion extending outwardly therefrom. The surgical buttress includes a proximal end portion and a distal end portion. The proximal end portion is positioned over the protrusion of the staple cartridge. The buttress retention band is disposed around the proximal end portion of the surgical buttress and the protrusion of the staple cartridge to releasably secure the proximal end portion of the surgical buttress to the staple cartridge assembly.

20 Claims, 8 Drawing Sheets

(52) U.S. Cl.
CPC ........ *A61B 17/068* (2013.01); *A61B 17/07207* (2013.01); *A61B 2017/07214* (2013.01); *A61B 2017/07257* (2013.01); *A61B 2017/07271* (2013.01)

(58) Field of Classification Search
USPC ..... 227/19, 176.1, 175.1, 180.1; 606/1, 139, 606/219
See application file for complete search history.

(56) References Cited

U.S. PATENT DOCUMENTS

| | | |
|---|---|---|
| 3,364,200 A | 1/1968 | Ashton et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,306,289 A | 4/1994 | Kaplan et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |

(56) References Cited

U.S. PATENT DOCUMENTS

| | | |
|---|---|---|
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,273,105 B2 | 9/2012 | Cohen et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |

(56) References Cited

U.S. PATENT DOCUMENTS

| | | |
|---|---|---|
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 11,510,670 B1 | 11/2022 | Baril et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |

(56) References Cited

U.S. PATENT DOCUMENTS

| | | |
|---|---|---|
| 2006/0173470 A1 | 8/2006 | Oray et al. |
| 2006/0190027 A1 | 8/2006 | Downey |
| 2007/0034669 A1 | 2/2007 | De La Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034922 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0116416 A1 | 5/2012 | Neff et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0138423 A1 | 5/2014 | Whitfield et al. |
| 2014/0224686 A1 | 8/2014 | Aronhalt et al. |
| 2014/0239470 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310134 A1 | 10/2016 | Contini et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |
| 2019/0254671 A1 | 8/2019 | Shankarsetty |
| 2019/0343522 A1 | 11/2019 | Williams |
| 2021/0177411 A1 | 6/2021 | Williams |
| 2021/0290227 A1 | 9/2021 | Mandula |
| 2021/0330326 A1 | 10/2021 | Taylor |
| 2022/0117600 A1 | 4/2022 | Abramek |
| 2022/0160356 A1 | 5/2022 | George |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2407114 A2 | 1/2012 |
| EP | 2491867 A1 | 8/2012 |
| EP | 3735911 A1 | 11/2020 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 9516221 A1 | 6/1995 |
| WO | 9838923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).

(56) References Cited

OTHER PUBLICATIONS

European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).

(56) References Cited

OTHER PUBLICATIONS

Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
International Search Report and Written Opinion issued in corresponding International Application No. PCT/IB2022/055591 dated Sep. 30, 2022, 12 pages.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.

(56) References Cited

OTHER PUBLICATIONS

European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.

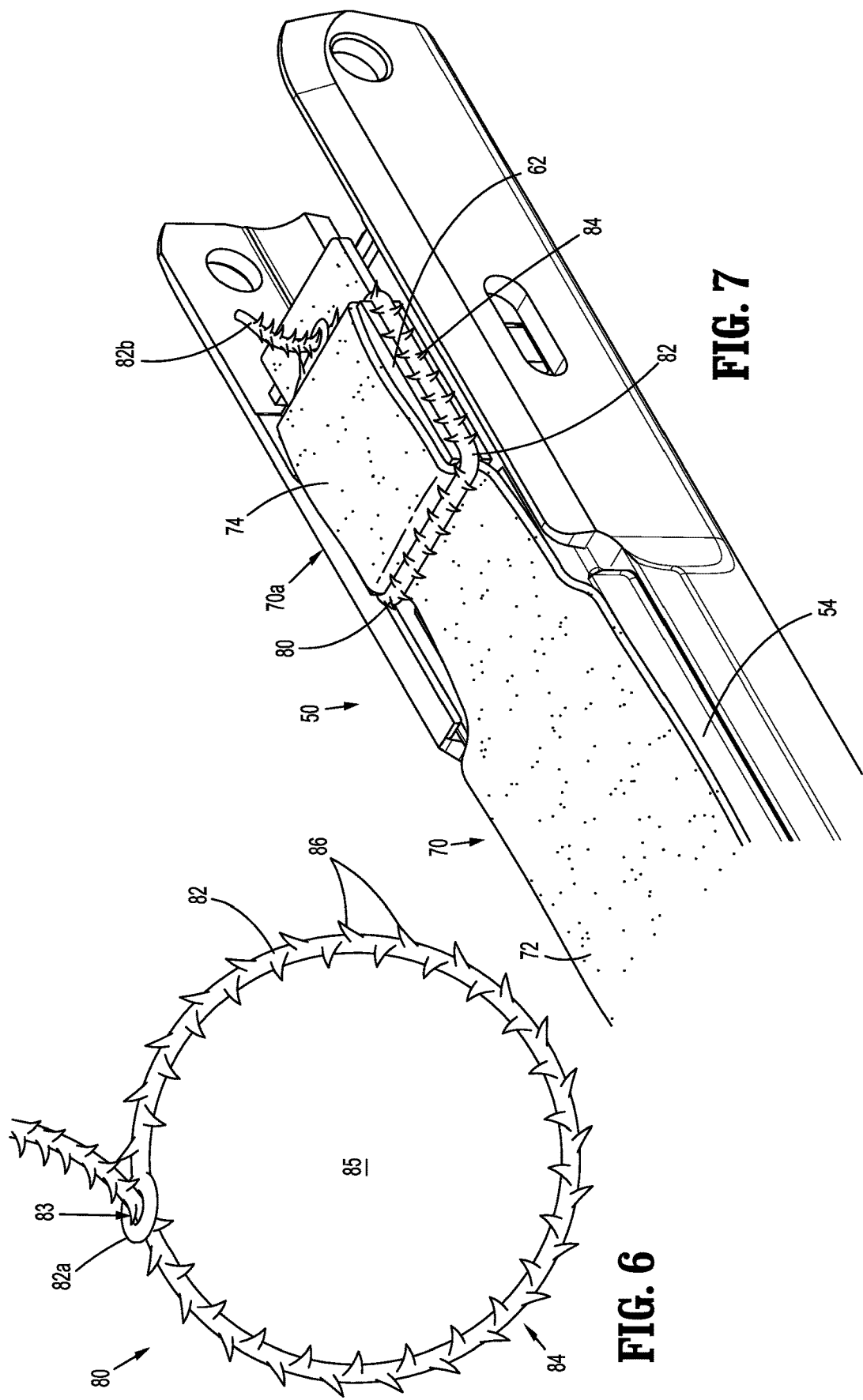

BUTTRESS ATTACHMENT FOR SURGICAL STAPLING APPARATUS

CROSS-REFERENCE TO RELATED APPLICATIONS

The present application is a continuation of U.S. patent application Ser. No. 17/355,240, filed Jun. 23, 2021, now U.S. Pat. No. 11,510,670 issued Nov. 29, 2022, the entire contents of which is incorporated by reference herein.

FIELD

The present application is generally related to surgical stapling apparatus, and more particularly, to surgical buttress attachment assemblies for releasably securing surgical buttresses to the surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together. Such apparatus generally include a pair of jaws or finger-like structures between which the body tissue to be joined is placed. When the surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon, e.g., by an expensive automated attachment process. The buttress material reinforces the staple or suture line as well as covers the juncture of the body tissues to reduce leakage prior to healing.

SUMMARY

The present disclosure relates to buttress material attachment onto a surgical stapling apparatus. Surgical buttress attachment assemblies of this disclosure are designed to make surgical buttress attachment in the operating room a simple, straightforward, and cost-effective procedure.

In one aspect, the present disclosure provides a surgical stapling apparatus including a loading unit, a surgical buttress, and a buttress retention band. The loading unit includes an anvil assembly and a staple cartridge assembly. The staple cartridge assembly includes a staple cartridge having a tissue facing surface including staple pockets and a central longitudinal slot defined therethrough, and a protrusion extending outwardly therefrom. The surgical buttress includes a proximal end portion and a distal end portion. The proximal end portion is positioned over the protrusion of the staple cartridge. The buttress retention band is disposed around the proximal end portion of the surgical buttress and the protrusion of the staple cartridge to releasably secure the proximal end portion of the surgical buttress to the staple cartridge assembly.

The protrusion of the staple cartridge may be disposed proximal to the staple pockets defined in the tissue facing surface of the staple cartridge. The protrusion may include sidewalls extending outwardly from the tissue facing surface and a platform raised off the tissue facing surface. In some aspects, the proximal end portion of the surgical buttress has a width that is the same as a width of the platform of the protrusion. The protrusion may include a groove extending around a periphery thereof, and the buttress retention band may be disposed within the groove. The protrusion may have a split body including first and second body halves disposed on opposed sides of the central longitudinal slot of the staple cartridge.

The proximal end portion of the surgical buttress may be a tab extending proximally from a body of the surgical buttress. The distal end portion of the surgical buttress may be a pocket extending distally from a body of the surgical buttress, and the staple cartridge may include a cartridge tip disposed within the pocket to releasably secure the distal end portion of the surgical buttress to the staple cartridge assembly. The pocket may include perforations defined therein. The perforations may be aligned with the central longitudinal slot of the staple cartridge.

The buttress retention band may include an elongate body having first and second ends. The first end may be slidably coupled onto the elongate body to form a loop encircling the proximal end portion of the surgical buttress and the protrusion of the staple cartridge. The first end of the elongate body may include an aperture through which the second end of the elongate body is threaded. The elongate body may include barbs. The buttress retention band may be threaded through the proximal end portion of the surgical buttress to form a loop around the proximal end portion.

The anvil assembly may include an anvil plate having a tissue facing surface including staple forming pockets and a central longitudinal slot defined therethrough, and a protrusion extending outwardly therefrom. In some aspects, the surgical stapling apparatus further includes a second surgical buttress and a second buttress retention band. The second surgical buttress includes a proximal end portion and a distal end portion. The proximal end portion is positioned over the protrusion of the anvil plate. The second buttress retention band is disposed around the proximal end portion of the second surgical buttress and the protrusion of the anvil plate to releasably secure the proximal end portion of the second surgical buttress to the anvil assembly. The protrusions of the anvil and staple cartridge assemblies may be disposed proximal to the staple forming pockets and the staple pockets.

The distal end portion of the second surgical buttress may include a pocket, and the anvil assembly may include an anvil tip disposed within the pocket to releasably secure the distal end portion of the second surgical buttress to the anvil assembly.

In another aspect, this disclosure provides a surgical buttress attachment assembly including a staple cartridge, a surgical buttress, and a buttress retention band. The staple cartridge has a tissue facing surface including staple pockets and a central longitudinal slot defined therethrough, and a protrusion extending outwardly therefrom. The surgical buttress includes a proximal end portion and a distal end portion. The proximal end portion is positioned over the protrusion of the staple cartridge. The buttress retention band is disposed around the proximal end portion of the surgical buttress and the protrusion of the staple cartridge to releasably secure the proximal end portion of the surgical buttress to the staple cartridge.

The distal end portion of the surgical buttress may include a pocket and the staple cartridge may include a cartridge tip disposed within the pocket to releasably secure the distal end portion of the surgical buttress to the staple cartridge.

The details of one or more aspects of this disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of the present disclosure are described hereinbelow with reference to the drawings, which are incorporated in and constitute a part of this specification, wherein:

FIG. 6 is a front view of the buttress retention band of FIG. 3;

FIG. 7 is a perspective view of a proximal end portion of the staple cartridge assembly of FIG. 3, shown with the surgical buttress secured to the staple cartridge by the buttress retention band;

DETAILED DESCRIPTION

Figure 1:
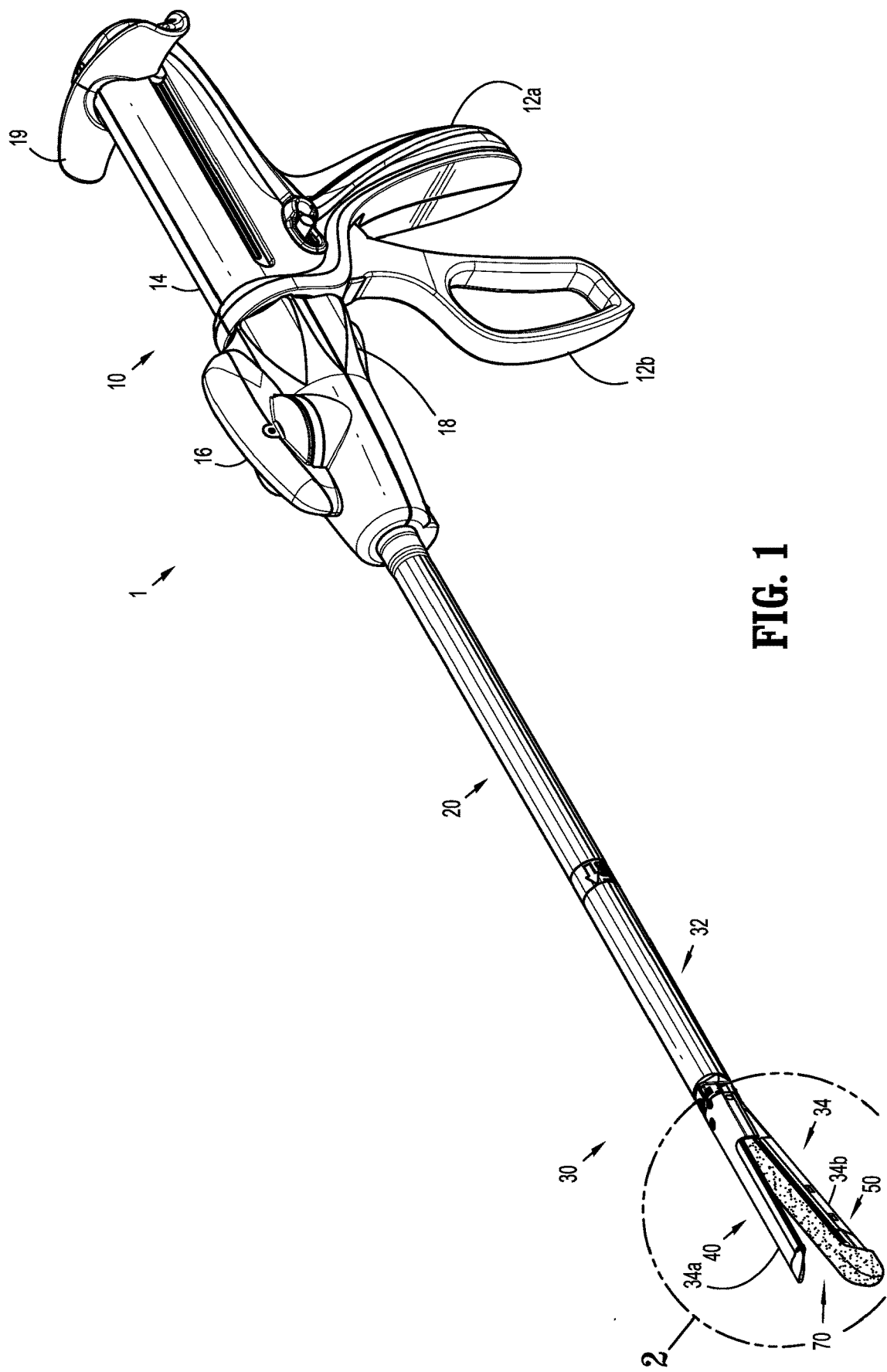
FIG. 1 is a perspective view of a surgical stapling apparatus in accordance with an aspect of the present disclosure.

Aspects of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user.

Referring now to FIG. 1, an exemplary surgical stapling apparatus or surgical stapler 1 is shown for use in stapling tissue in accordance with aspects of the present disclosure. The surgical stapling apparatus 1 generally includes a handle assembly 10, an elongate tubular body 20 extending distally from the handle assembly 10, and a loading unit 30 extending distally from the elongate tubular body 20. The loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other.

The handle assembly 10 includes a stationary handle member 12a, a movable handle member 12b, and a barrel portion 14. Actuation of the movable handle member 12b applies lines of staples to tissue captured between the first and second jaw members 34a, 34b of the tool assembly 34. An articulation lever 16 is mounted on the forward end of the barrel portion 14 to facilitate articulation of the tool assembly 34. A rotatable member 18 is also mounted on the forward end of the barrel portion 14, adjacent the articulation lever 16. Rotation of the rotatable member 18 relative to the barrel portion 14 rotates the elongate tubular body 20 and the loading unit 30 relative to the handle assembly 10 so as to properly orient the tool assembly 34 relative to tissue to be stapled. A knob 19 is movably positionable along the barrel portion 14. The knob 19 is advanced distally to approximate or close the first and second jaw members 34a, 34b of the tool assembly 34 relative to each other, and retracted proximally to unapproximate or open the first and second jaw members 34a, 34b of the tool assembly 34 with respect to each other.

Figure 2:
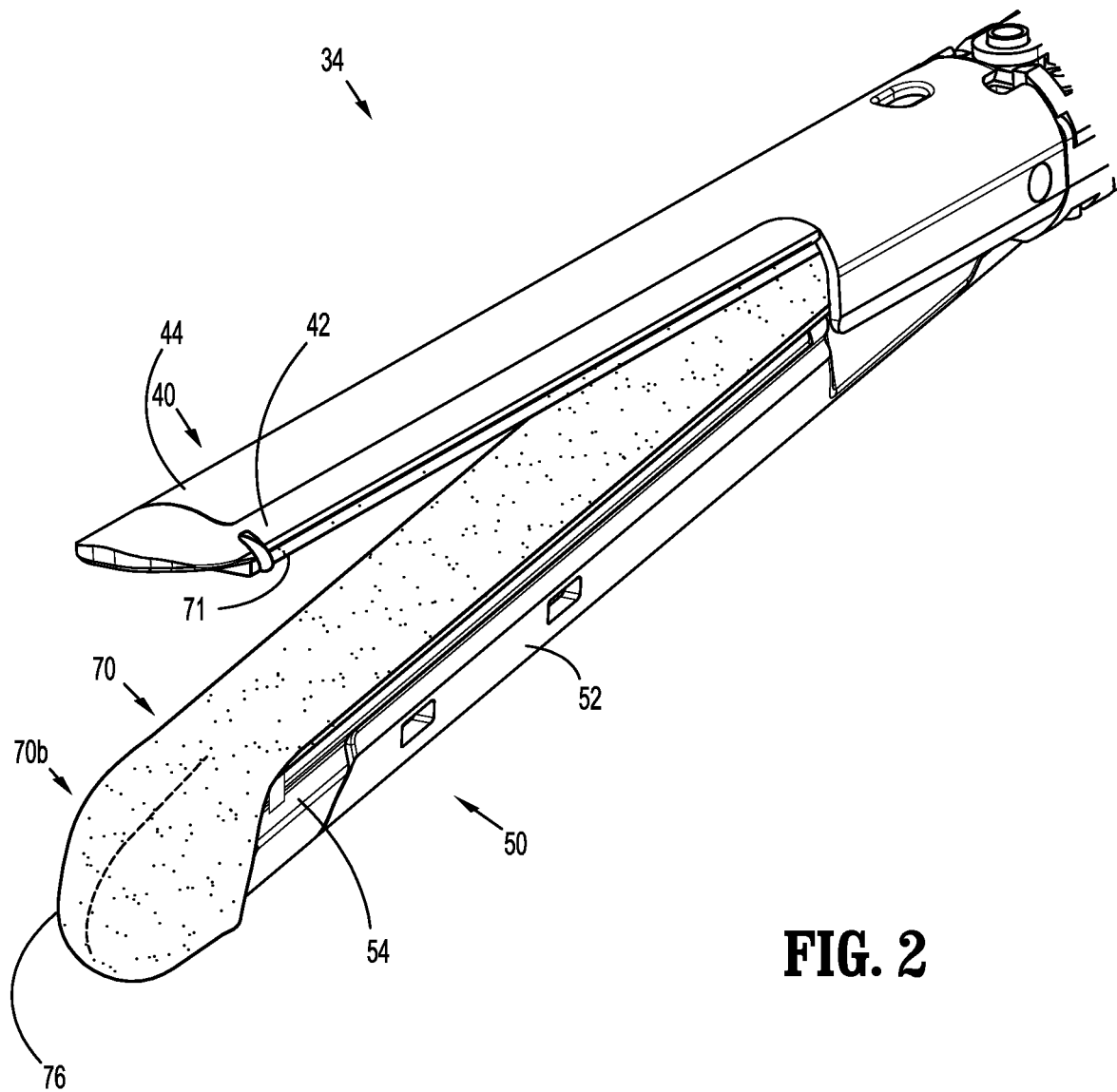
FIG. 2 is a close-up view of the area of detail 2 indicated in FIG. 1, showing a tool assembly of the surgical stapling apparatus.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly (e.g., a staple cartridge 54 as seen in FIG. 2) of the MULU is replaced after each staple and cut operation of the surgical stapling apparatus 1 a pre-determined number of times before the entire MULU needs to be replaced. Alternatively, the loading unit 30 may be permanently affixed to the elongated tubular body 20.

As shown in FIGS. 1 and 2, the first jaw member 34a of the tool assembly 34 includes an anvil assembly 40 and the second jaw member 34b of the tool assembly 34 includes a staple cartridge assembly 50. The anvil assembly 40 includes an anvil plate 42 and a cover plate 44 secured over the anvil plate 42. The staple cartridge assembly 50 includes a cartridge carrier 52 and a staple cartridge 54 selectively received and supported within the cartridge carrier 52. The staple cartridge 54 may be removably and/or replaceably attached to the cartridge carrier 52 by, for example, a snap-fit connection, a detent, a latch, among other types of connectors within the purview of those skilled in the art.

For a detailed description of the structure and function of exemplary surgical stapling apparatus, reference may be made to U.S. Pat. Nos. 6,241,139, 6,330,965, and 7,819,896, the entire contents of each of which are incorporated herein by reference. It should be appreciated that principles of the present disclosure are equally applicable to surgical stapling apparatus having other configurations such as, for example, the types described in U.S. Pat. Nos. 5,964,394, 7,128,253, and 7,334,717, the entire contents of each of which are incorporated herein by reference. Accordingly, it should be understood that a variety of surgical stapling apparatus may be utilized with aspects of the present disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, CT) may be utilized with aspects of the present disclosure.

Figure 3:
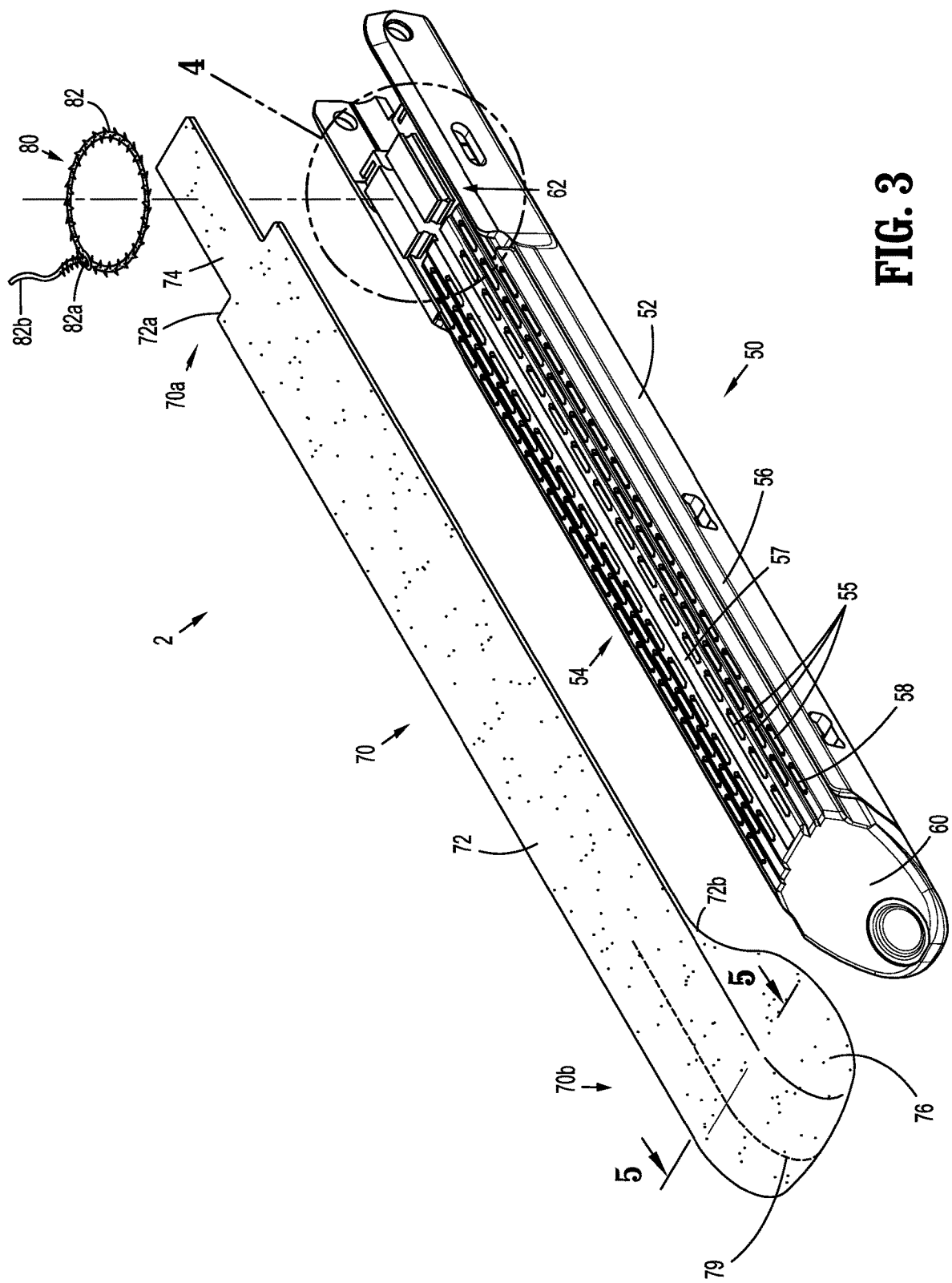
FIG. 3 is a perspective view, with parts separated, of a surgical buttress attachment assembly including a surgical buttress, a buttress retention band, and a staple cartridge assembly of the surgical stapling apparatus of FIG. 1.

Turning now to FIG. 3, a surgical buttress attachment assembly 2 of the surgical stapling apparatus 1 (FIG. 1) is shown. The surgical buttress attachment assembly 2 includes the staple cartridge assembly 50, a surgical buttress 70, and a buttress retention band 80.

The staple cartridge 54 of the staple cartridge assembly 50 includes a cartridge body 56 having an inward or tissue facing surface 58 defining staple pockets or retention slots 55 formed therein. A central longitudinal slot 57 is formed in and extends along a substantial length of the cartridge body 56 to facilitate passage of a knife blade 24 (FIG. 8) of a drive assembly 22 therethrough. A cartridge tip 60 extends axially from the cartridge body 56 distal to the staple pockets 55 and a protrusion 62 extends outwardly from the tissue facing surface 58 of the cartridge body 56 proximal to the staple pockets 55.

Figure 4:
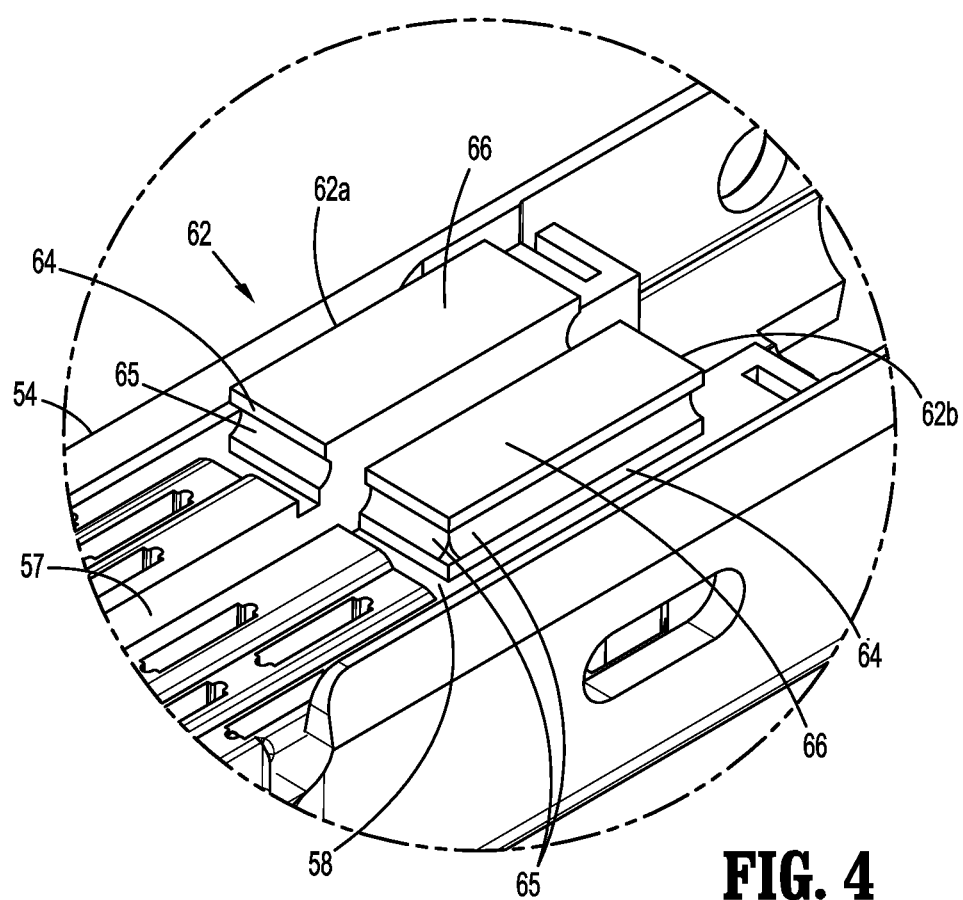
FIG. 4 is a close-up view of the area of detail 4 indicated in FIG. 3, showing a proximal end portion of the staple cartridge assembly.

As shown in FIGS. 3 and 4, the protrusion 62 is a projection, bump, protuberance, etc. on the tissue facing surface 58 of the staple cartridge 54 to which a proximal end portion 70a of the surgical buttress 70 is releasably secured via the buttress retention band 80. The protrusion 62 has a split body including first and second body halves 62a, 62b disposed on opposed sides of the central longitudinal slot 57 of the staple cartridge 54 so that the protrusion 62 does not encumber travel of the knife blade 24 (FIG. 8) during a firing stroke of the surgical stapling apparatus 1 (FIG. 1). The protrusion 62 includes side walls 64 extending outwardly from the tissue facing surface 58 of the staple cartridge 54 towards the anvil assembly 40 (FIG. 2) and a platform 66 raised off of the tissue facing surface 58 and extending along a plane parallel to a plane defined by the tissue facing surface 58. A groove 65 is defined in the side walls 64 and extends around a periphery of the protrusion 62 (e.g., circumferentially therearound).

With continued reference to FIG. 3, the surgical buttress 70 includes a body 72 having a generally rectangular shape that is configured for positioning over the staple pockets 55 of the tissue facing surface 58 of the staple cartridge 54. A proximal end portion 70a of the surgical buttress 70 includes a tab 74 and a distal end portion 70b of the surgical buttress 70 includes a pocket 76. The tab 74 extends proximally from a proximal end 72a of the body 72 and is sized and shaped for positioning over the protrusion 62 on the tissue facing surface 58 of the staple cartridge 54. In aspects, the tab 74 has a width that is smaller than a width of the body 72 and, in some aspects, the tab 74 has a width that is substantially the same as a width of the protrusion 62 of the staple cartridge 54. In aspects, the tab 74 has a length that is longer than a length of the protrusion 62 such that the tab 74 covers the protrusion 62 along the length thereof.

Figure 5:
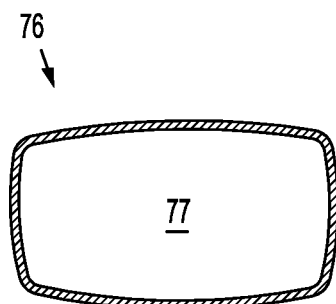
FIG. 5 is a cross-sectional view of the surgical buttress of FIG. 3, taken along section line 5-5 of FIG. 3.

As shown in FIGS. 3 and 5, the pocket 76 extends distally from a distal end 72b of the body 72 and is sized and shaped for positioning around the cartridge tip 60 of the staple cartridge 54. The pocket 76 has a proximally facing opening into a cavity 77 defined therein for receiving the cartridge tip 60. Perforations 79 are defined in the pocket 76 and extend along a plane coincident with the central longitudinal slot 57 of the staple cartridge 54 when the surgical buttress 70 is disposed on the staple cartridge assembly 50. In some aspects, the perforations 79 are disposed distal to the central longitudinal slot 57 of the staple cartridge 54 (e.g., only in the pocket 76 of the surgical buttress 70) and, in some other aspects, the perforations 79 are further defined in the body 72 of the surgical buttress 70 (e.g., in the distal end 72b of the body 72) and overlie a portion of the central longitudinal slot 57.

The surgical buttress 70 is fabricated from biocompatible materials which are bioabsorbable or non-absorbable, natural or synthetic materials. It should be understood that a single or combination of natural, synthetic, bioabsorbable, and/or non-bioabsorbable materials may be used to form the surgical buttress 70. In aspects, the surgical buttress 70 is a single sheet of material that is formed and cut to shape. In other aspects, the surgical buttress 70 is formed from a plurality of sheets of material, that are fabricated from the same or different materials, and/or the components (e.g., the body, the tab, the pocket, etc.) of the surgical buttress 70 are formed from the same or different materials that are attached to one another by, for example, welding, using adhesive, tying sutures, etc.

The surgical buttress 70 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttress 70 may be a single porous or non-porous layer, or include a plurality of layers including any combination of porous and non-porous layers. For example, the surgical buttress 70 may include multiple porous and non-porous layers that are stacked in an alternating manner. In another example, the surgical buttress 70 may be formed in a "sandwich-like" manner wherein the outer layers are porous and the inner layer(s) are non-porous, or vice versa.

Porous layer(s) in the surgical buttress 70 may enhance the ability of the surgical buttress 70 to absorb fluid, reduce bleeding, and/or seal a wound. Also, the porous layer(s) may allow for tissue ingrowth to fix the surgical buttress 70 in place. Non-porous layer(s) in the surgical buttress 70 may enhance the ability of the surgical buttress 70 to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

As shown in FIGS. 3 and 6, the buttress retention band 80 has an elongate body 82 including first and second ends 82a, 82b. The elongate body 82 is formed from a length of material (e.g., a single, continuous structure, such as a suture, a thread, a fiber, etc. having a monofilament or multifilament construction). The first end 82a of the elongate body 82 is slidably coupled onto the elongate body 82 to form a loop 84 defining an opening 85 therein that is adjustable in size. The first end 82a includes an aperture 83 through which the second end 82b is threaded. The second end 82b can be moved relative to the aperture 83 to adjust the size of the loop 84. The loop 84 is configured to encircle and grip the protrusion 62 of the staple cartridge 54.

The elongate body 82 includes barbs 86 along a majority thereof, with the first end 82a of the elongate body 82 being barbless to provide a surface to which the barbs 86 adhere and the second end 82b of the elongate body 82 also being barbless to provide a grasping portion for the user. The barbs 86 help facilitate locking of the loop 84 once adjusted to a desired sized and, in aspects, allows for one-way travel of the elongate body 82 through the first end 82a for adjusting the loop 84 to a smaller size. The barbs 86 may be single or compound and may be oriented in a unidirectional or bidirectional arrangement. For example, a barbed suture available commercially as V-LOC™ from Medtronic (North Haven, CT) may be utilized with aspects of the present disclosure. For a detailed description of the structure and function of exemplary sutures suitable for use as buttress retention bands, reference may be made to U.S. Pat. Nos. 5,306,289 and 8,273,105, the entire contents of each of which are incorporated herein by reference. It should be understood that the buttress retention band may have other barb configurations, such as barbs along portion(s) or the entirety thereof. Alternatively, the buttress retention band may be barbless.

The buttress retention band 80 is formed from biocompatible materials which may be any combination of natural, synthetic, bioabsorbable, and/or non-bioabsorbable materials. In aspects, the buttress retention band 80 is formed from a biodegradable material such that any portion released into the body of a patient (e.g., fragments remaining with the surgical buttress 70 or cut after firing of the surgical stapling apparatus 1) does not need to be retrieved from the patient's body. It is envisioned that the buttress retention band 80 may be formed from an elastic or stretchable material having a pre-formed, continuous loop biased in size to engage the protrusion 62 of the staple cartridge assembly 50, and stretchable during placement on the protrusion 62.

With continued reference to FIGS. 3-6, in a method of loading the surgical buttress 70 onto the staple cartridge assembly 50, the pocket 76 of the surgical buttress 70 is aligned with the cartridge tip 60 of the staple cartridge assembly 50 and slid thereover such that the cartridge tip 60 is received and retained within the cavity 77 defined in the pocket 76 of the surgical buttress 70, as seen in FIG. 2. The body 72 of the surgical buttress 70 is laid against the tissue facing surface 58 of the staple cartridge 54, with the tab 74 of the surgical buttress 70 aligned with and extending across the platform 66 of the protrusion 62 of the staple cartridge 54. The buttress retention band 80 is placed over the tab 74 of the surgical buttress 70 with the loop 84 encircling the tab 74 and the protrusion 62. The buttress retention band 80 is then tightened by pulling the second end 82b of the elongate body 82 to adjust the size of the loop 84 and to capture the tab 74 of the surgical buttress 70 onto the projection 62 of the staple cartridge 54, as seen in FIG. 7. In aspects, buttress retention band 80 is aligned with the groove 65 defined in the protrusion 62 such that the elongate body 82 is fixed within the groove 65 during tightening of the loop 84 to secure the buttress retention band 80 to the tab 74 and the projection 62.

Accordingly, the proximal end portion 70a of the surgical buttress 70 is retained on the staple cartridge assembly 50 by engagement of the tab 74 with the protrusion 62 via the buttress retention band 80 (FIG. 7), and the distal end portion 70b of the surgical buttress 70 is retained on the staple cartridge assembly 50 by engagement of the pocket 76 with the cartridge tip 60 (FIG. 2).

The surgical stapling apparatus 1 (FIG. 1), with the staple cartridge assembly 50 loaded with the surgical buttress 70, is ready for use. In aspects, as seen in FIG. 2, the anvil assembly 40 is pre-loaded and/or loaded with a surgical buttress 71. The surgical buttress 71 is retained on the anvil assembly 40 by any suitable attachment feature within the purview of those skilled in the art, such as, for example, mechanical attachment features (e.g., a suture as seen in FIG. 2), chemical attachment features (e.g., adhesive), and/or attachment methods (e.g., welding).

Figure 8:
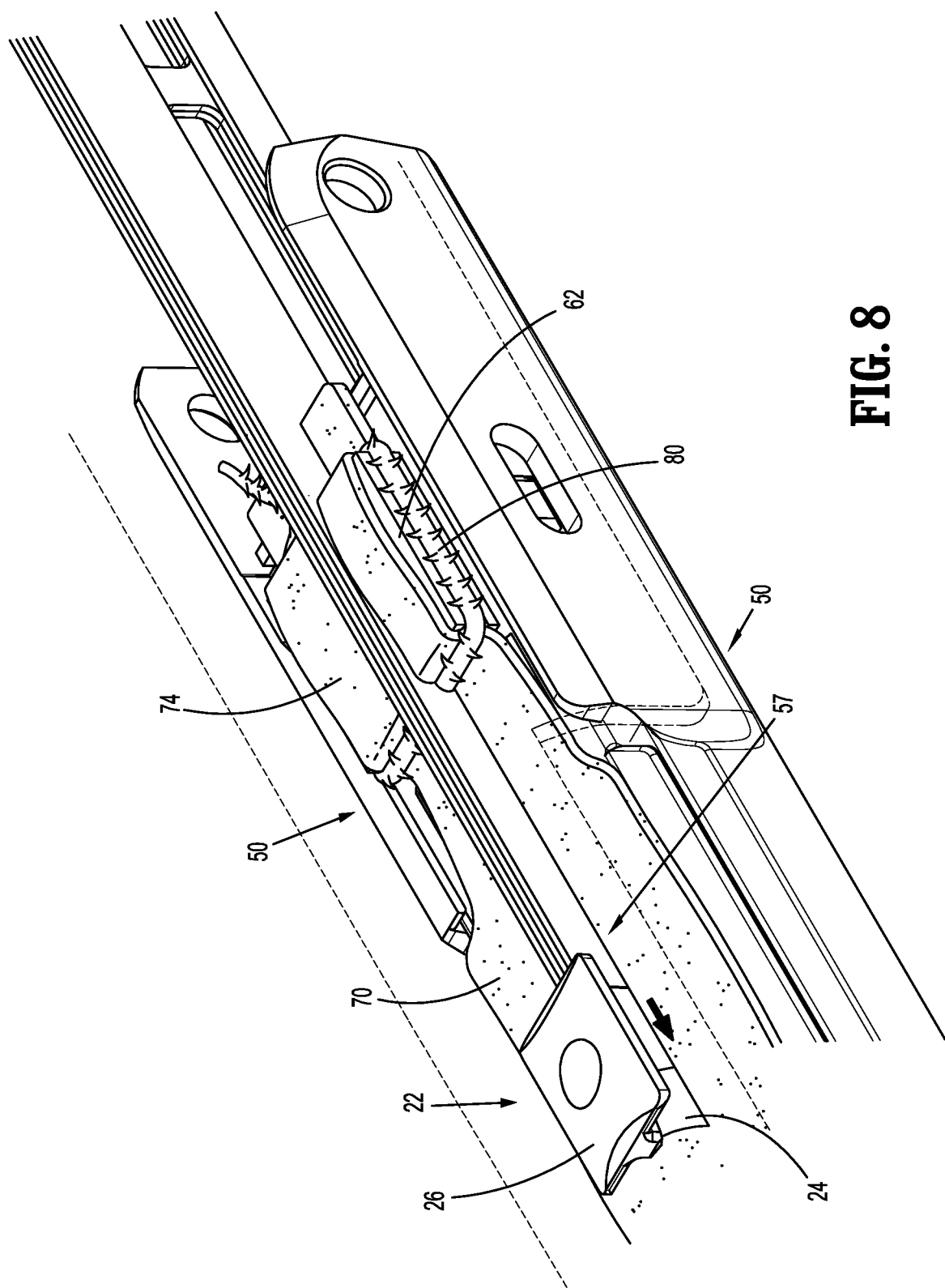
FIG. 8 is a perspective view of the proximal end portion of the staple cartridge assembly of FIG. 7, shown during a firing stroke of the surgical stapling apparatus.

In operation, with the loading unit 30 loaded with the surgical buttress 70, as described above and shown in FIG. 1, the surgical stapling apparatus 1 is used in accordance with methods known by those skilled in the art. Once the anvil and staple cartridge assemblies 40, 50 are clamped onto tissue, the surgical stapling apparatus 1 is fired, thereby stapling the surgical buttress 70 to the tissue. As shown in FIG. 8, during firing, the knife blade 24 of the drive assembly 22, which is defined in a distal edge of an I-beam 26, travels distally through the central longitudinal slot 57 and substantially simultaneously cuts and divides the tissue and the surgical buttress 70 disposed between the rows of formed staples. Specifically, the knife blade 24 travels through the protrusion 62 and cuts the buttress retention band 80 thereby releasing the tab 74 from the protrusion 62. When firing is complete and the anvil and staple cartridge assemblies 40, 50 are unclamped, the surgical buttress 70, which is now stapled to the tissue, pulls away from the staple cartridge assembly 50, and the tool assembly 34 can be removed from the surgical site. Specifically, the tab 74 of the surgical buttress 70 is freed from the protrusion 62 by cutting of the buttress retention band 80, and the pocket 76 of the surgical buttress 70 is freed from the cartridge tip 60 by tearing of the pocket 76 along the perforations 79 as the surgical buttress 70 pulls away from the staple cartridge 54. The used staple cartridge 54 may then be removed from the tool assembly 34 and replaced with a new staple cartridge 54. A new surgical buttress 70 may be installed onto the staple cartridge assembly 50, as needed or desired, as described above.

Figure 9:
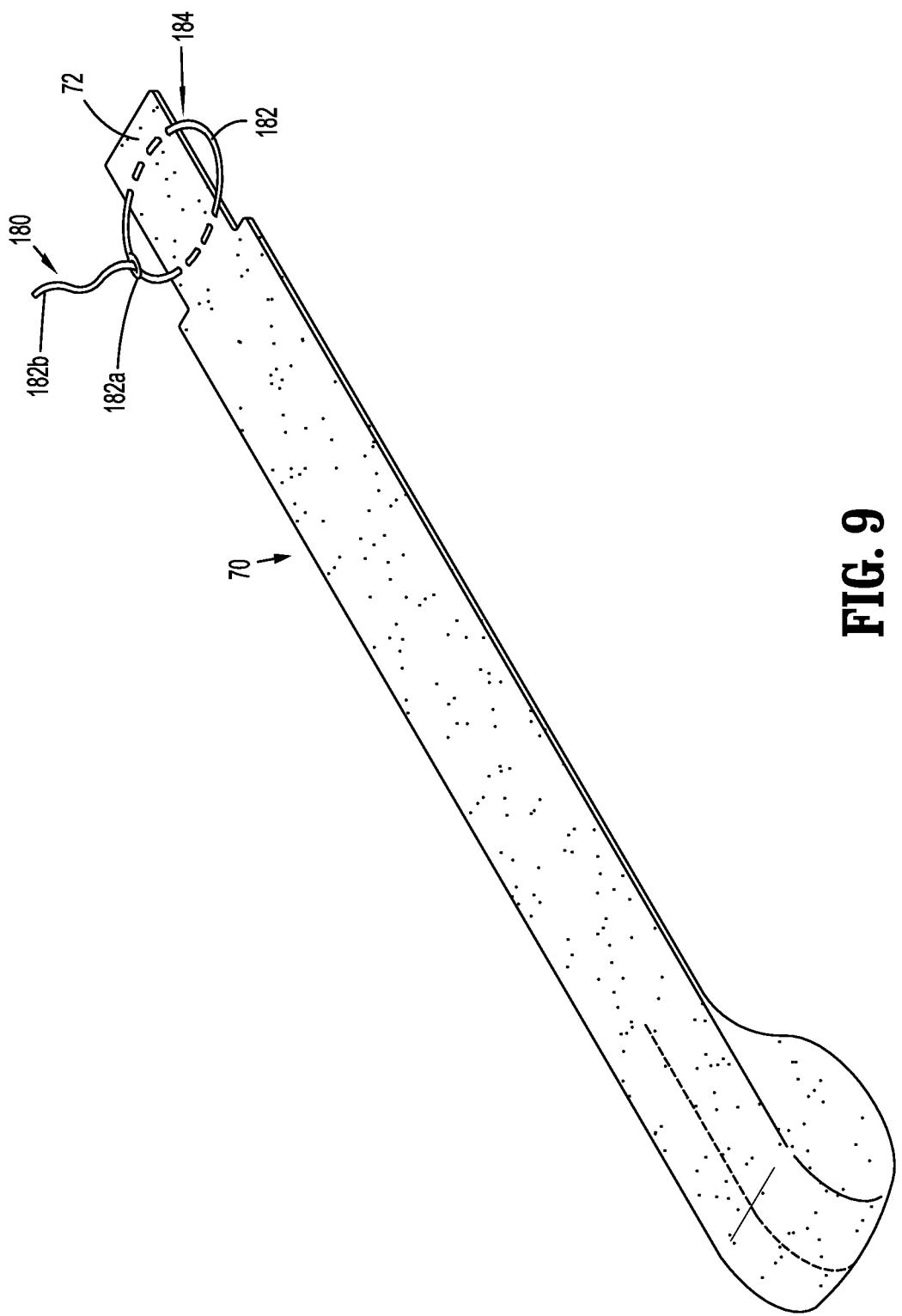
FIG. 9 is a perspective view of a surgical buttress and a buttress retention band in accordance with another aspect of the present disclosure.

As shown in FIG. 9, the surgical buttress 70 and a buttress retention band 180 may be assembled together prior to securing the surgical buttress 70 to the staple cartridge assembly 50 (FIG. 3). The buttress retention band 180 is substantially the same as the buttress retention band 80 of FIG. 3, except that the elongate body 182 is free of barbs. It should be understood, however, that the buttress retention band 180 may include barbs along a portion or the entirety thereof. The buttress retention band 180 is pre-threaded or weaved through the tab 72 of the surgical buttress 70 such that when the surgical buttress 70 is loaded onto the staple cartridge assembly 50, the tab 72 and the buttress retention band 180 are in registration with the protrusion 62 (FIG. 3) of the staple cartridge assembly 50 and can be tightened thereon. In some aspects, the first end 182a of the elongate body 182 includes a knot that tightens as the second end 182b is pulled therethrough and, in some other aspects, the buttress retention band 180 may be tied after tightening of the loop 184.

Figure 10:
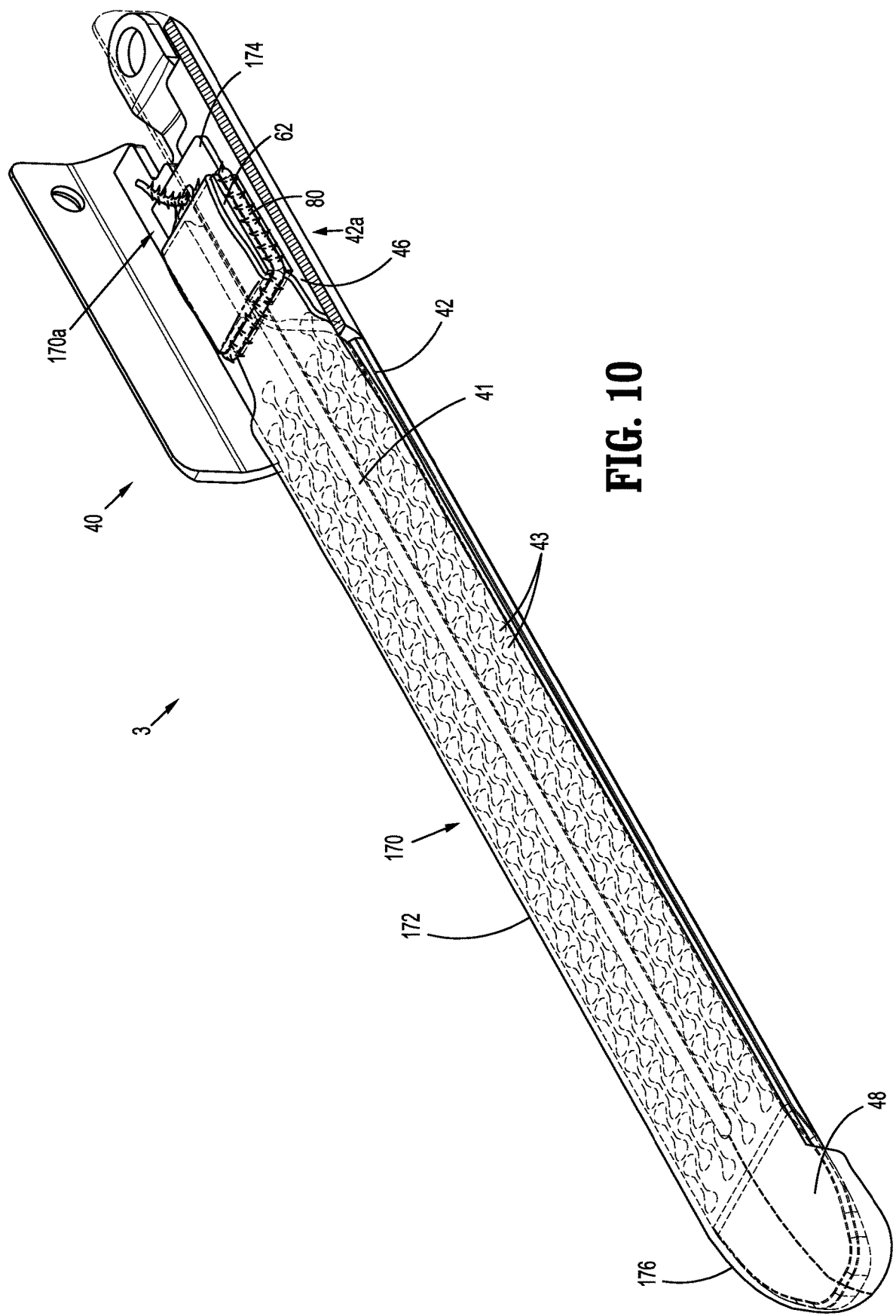
FIG. 10 is a bottom, perspective view of a surgical buttress attachment assembly including a surgical buttress, a buttress retention band, and an anvil assembly in accordance with another aspect of the present disclosure.

While the staple cartridge assembly 50 is shown as part of the surgical buttress retention assembly 2, it should be understood that the anvil assembly 40 may be part of a surgical buttress retention assembly. As shown in FIG. 10, a surgical buttress attachment assembly 3 includes the anvil assembly 40, a surgical buttress 170, and a buttress retention band 80. The surgical buttress assembly 3 may be used in addition or as an alternative to the surgical buttress assembly 2 (FIG. 3) on the surgical stapling apparatus 1 (FIG. 1).

As shown in FIG. 10, the anvil assembly 40 has a central longitudinal slot 41 formed in the anvil plate 42 and a plurality of staple forming pockets or cavities 43 defined in an inward or tissue facing surface thereof 46. An anvil tip 48 extends distal to the staple forming pockets 43. A proximal portion 42a of the anvil plate 42, which extends proximally of the staple forming pockets 43, includes a projection 62 configured to secure a proximal end portion 170a of the surgical buttress 170 thereto. The surgical buttress 170 is substantially the same as the surgical buttress 70 of FIG. 3, except that the pocket 176 is sized and shaped to accommodate the anvil tip 48, and the length of the body 172 and/or the tab 174 may vary depending upon the position of the protrusion 62 relative to the anvil tip 48. In aspects in which both the anvil and staple cartridge assemblies 40, 50 include a projection 62, the projections 62 are disposed adjacent to each other in longitudinally spaced relation so as not to interfere with opening and closing of the first and second jaw members 34a, 34b (FIG. 1).

While illustrated as being used on a hand-held manually actuated surgical device hereinabove, it is contemplated, and within the scope of the present disclosure for the loading unit 30 to be configured for use with various electromechanical surgical instruments and/or electrosurgical instruments. For example, the loading unit 30 may be configured to be detachably coupleable and controllable by a handheld electromechanical surgical device, such as the handheld electromechanical surgical system shown and described in U.S. Patent Appl. Pub. No. 2016/0310134, the entire content of which is incorporated herein by reference. As another example, the loading unit 30 may be configured to detachably coupleable and controllable by a robotic surgical system, such as the robotic surgical system shown and described in U.S. Patent Appl. Pub. No. 2012/0116416, the entire content of which is incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical stapling apparatus comprising:
   a loading unit including an anvil assembly and a staple cartridge assembly, the anvil assembly including a tissue facing surface having a protrusion extending outwardly therefrom;
   a surgical buttress including a proximal end portion and a distal end portion, the proximal end portion positioned over the protrusion of the anvil assembly; and
   a buttress retention band disposed around the proximal end portion of the surgical buttress and the protrusion of the anvil assembly to releasably secure the proximal end portion of the surgical buttress to the anvil assembly.

2. The surgical stapling apparatus according to claim 1, wherein the anvil assembly includes staple forming pockets defined in the tissue facing surface, and the protrusion is disposed proximal to the staple forming pockets.

3. The surgical stapling apparatus according to claim 1, wherein the protrusion includes sidewalls extending outwardly from the tissue facing surface and a platform raised off the tissue facing surface.

4. The surgical stapling apparatus according to claim 1, wherein the protrusion includes a groove extending around a periphery thereof, and the buttress retention band is disposed to secure the surgical buttress within the groove.

5. The surgical stapling apparatus according to claim 1, wherein the anvil assembly includes a central longitudinal slot formed through the tissue facing surface, and the protrusion has a split body including first and second body halves disposed on opposed sides of the central longitudinal slot.

6. The surgical stapling apparatus according to claim 1, wherein the proximal end portion of the surgical buttress has a width that is the same as a width of the protrusion.

7. The surgical stapling apparatus according to claim 1, wherein the proximal end portion of the surgical buttress includes a tab extending proximally from a body of the surgical buttress.

8. The surgical stapling apparatus according to claim 1, wherein the distal end portion of the surgical buttress includes a pocket extending distally from a body of the surgical buttress, and the anvil assembly includes an anvil tip disposed within the pocket to releasably secure the distal end portion of the surgical buttress to the anvil assembly.

9. The surgical stapling apparatus according to claim 8, wherein the pocket includes perforations defined therein.

10. The surgical stapling apparatus according to claim 9, wherein the anvil assembly includes a central longitudinal slot formed through the tissue facing surface, and the perforations are aligned with the central longitudinal slot.

11. The surgical stapling apparatus according to claim 1, wherein the buttress retention band includes an elongate body having first and second ends, the first end slidably coupled onto the elongate body to form a loop encircling the proximal end portion of the surgical buttress and the protrusion of the anvil assembly.

12. The surgical stapling apparatus according to claim 11, wherein the first end of the elongate body includes an aperture through which the second end of the elongate body is threaded.

13. The surgical stapling apparatus according to claim 1, wherein the buttress retention band includes barbs.

14. The surgical stapling apparatus according to claim 1, wherein the buttress retention band is threaded through the proximal end portion of the surgical buttress to form a loop around the proximal end portion.

15. The surgical stapling apparatus according to claim 1, wherein the buttress retention band is a pre-formed, continuous loop of stretchable material.

16. The surgical stapling apparatus according to claim 1, wherein the staple cartridge assembly has a tissue facing surface and a protrusion extending outwardly therefrom, and the surgical stapling apparatus further comprises:
   a second surgical buttress including a proximal end portion and a distal end portion, the proximal end portion positioned over the protrusion of the staple cartridge assembly; and
   a second buttress retention band disposed around the proximal end portion of the second surgical buttress and the protrusion of the staple cartridge assembly to releasably secure the proximal end portion of the second surgical buttress to the staple cartridge assembly.

17. The surgical stapling apparatus according to claim 16, wherein the protrusions of the anvil and staple cartridge assemblies are longitudinally offset with respect to each other.

18. The surgical stapling apparatus according to claim 16, wherein the anvil assembly includes staple forming pockets defined in the tissue facing surface of the anvil assembly and the staple cartridge assembly includes staple pockets defined in the tissue facing surface of the staple cartridge assembly, and the protrusions of the anvil and staple cartridge assemblies are proximal to the staple forming pockets and the staple pockets.

19. A surgical buttress attachment assembly comprising:
- an anvil assembly having a tissue facing surface including a protrusion extending outwardly therefrom;
- a surgical buttress including a proximal end portion and a distal end portion, the proximal end portion positioned over the protrusion of the anvil assembly; and
- a buttress retention band disposed around the proximal end portion of the surgical buttress and the protrusion of the anvil assembly to releasably secure the proximal end portion of the surgical buttress to the anvil assembly.

20. The surgical buttress attachment assembly according to claim 19, wherein the distal end portion of the surgical buttress includes a pocket, and the anvil assembly includes an anvil tip disposed within the pocket to releasably secure the distal end portion of the surgical buttress to the anvil assembly.

\* \* \* \* \*